Figure 1:
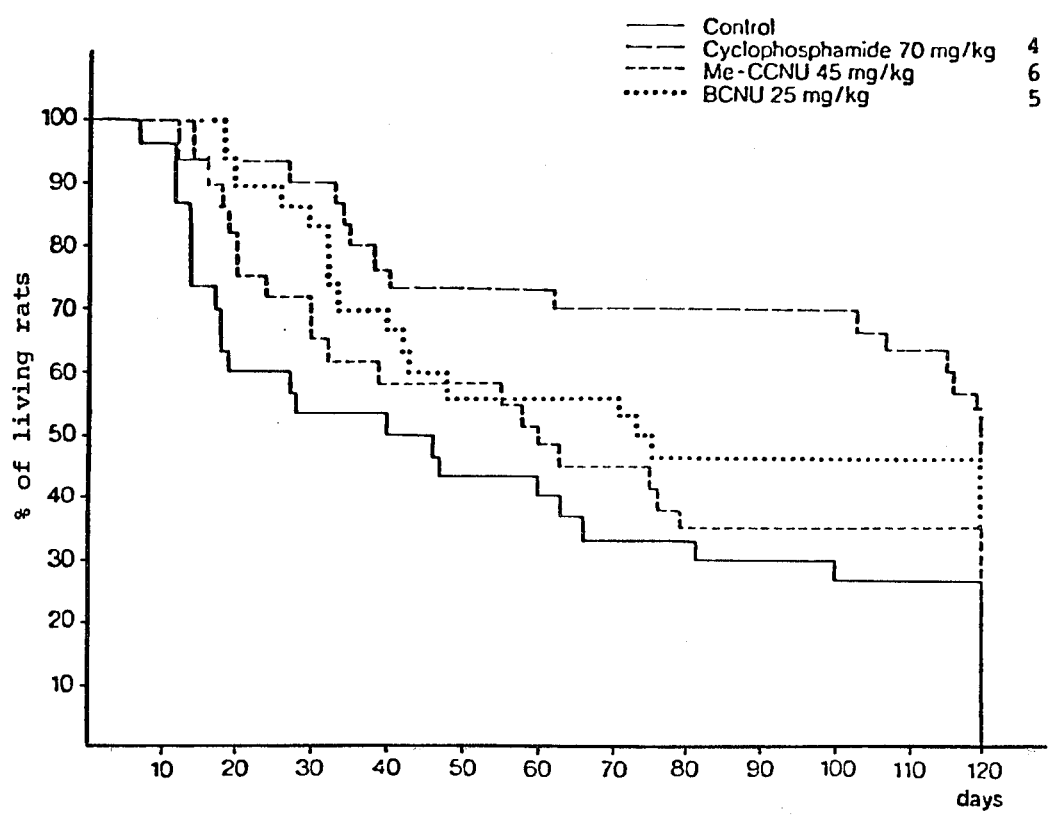

United States Patent [19]

Eisenbrand

[11] 4,377,687
[45] Mar. 22, 1983

[54] ANALOGS OF 1-(2-CHLOROETHYL)-1-NITROSO-3-(CYCLOHEYL)-UREA SUBSTITUTED BY HETEROCYCLIC RINGS OR ALKYL RADICALS

[75] Inventor: Gerhard Eisenbrand, Sandhausen, Fed. Rep. of Germany

[73] Assignee: Stiftung Deutsches Krebsforschungszentrum, Heidelberg, Fed. Rep. of Germany

[21] Appl. No.: 256,558

[22] Filed: Apr. 22, 1981

Related U.S. Application Data

[63] Continuation-in-part of Ser. No. 83,855, Oct. 11, 1979, abandoned.

[30] Foreign Application Priority Data

Oct. 19, 1978 [DE] Fed. Rep. of Germany ....... 2845574

[51] Int. Cl.$^3$ .................. C07D 295/22; C07C 133/02
[52] U.S. Cl. .................................... 544/164; 546/242; 546/243; 546/244; 564/33
[58] Field of Search ................. 544/164; 546/242, 243, 546/244; 260/454 A, 239 BF; 562/560; 564/33; 360/169

[56] References Cited

FOREIGN PATENT DOCUMENTS 2623420 5/1978 Fed. Rep. of Germany .

OTHER PUBLICATIONS

Eisenbrand, Chemical Abstracts, vol. 93 (1980) No. 132, 466m (Abstract of Germ. Offen, 2,845,574, Apr. 24, 1980).

Eisenbrand et al., J. Cancer Res. Clin. Oncol. vol. 95 (1979) pp. 43-49.

Primary Examiner—Robert W. Ramsuer

Attorney, Agent, or Firm—Murray Schaffer

[57] ABSTRACT

This invention relates to compounds having the formula:

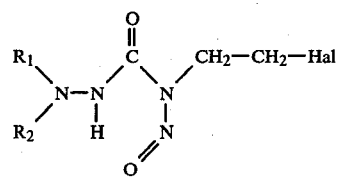

wherein $R_1$ and $R_2$ are selected from the group consisting of hydrogen, acyl, trifluoroacetyl, straight chained and branched alkyl groups with up to 6 carbon atoms, such alkyl groups with up to 3 substituents selected from the group consisting of OH, $OSO_2CH_3$, COOH, COOR, $CONH_2$ and Hal, where R is an alkyl group with up to 6 carbon atoms, and $R_1$ and $R_2$ together form a heterocyclic ring containing 4 to 6 carbon atoms and optionally further heteroatoms and such rings with up to 3 substituents selected from the group consisting of lower alkyl, OH, COOH, COOR, $CONH_2$, where R has the above meaning, the chloroethyl nitrosoureido group and Hal, and Hal is selected from the group consisting of chlorine and fluorine, which heterocyclic ring is not the para-methyl piperazine group, said nitroso ureas having a tumor inhibiting effect.

This invention also related to a method of inhibiting transplanted tumors which comprises treating a tumor-afflicted subject with one of the foregoing 1,3 - disubstituted nitroso ureas. It also involves a method of preparing such new compounds by reacting N-(2-halogenethyl)-N-nitrosocarbamoylazide with hydrazine or a monocyclic N-amino heterocyclic or their derivatives.

11 Claims, 4 Drawing Figures

Mortality of treated animals compared with untreated controls (experiment 1)

Mortality of treated animals compared with untreated controls (experiment 2)

Mortality of treated animals compared with untreated controls (experiment 3)

Mortality of treated animals compared with untreated controls (experiment 5)

ANALOGS OF 1-(2-CHLOROETHYL)-1-NITROSO-3-(CYCLOHEYL)-UREA SUBSTITUTED BY HETEROCYCLIC RINGS OR ALKYL RADICALS

RELATED APPLICATION

This application is a continuation-in-part of application Ser. No. 083,855, filed Oct. 11, 1979 abandoned.

DESCRIPTION OF THE INVENTION

The synthesis of unsymmetrical 1,3-disubstituted nitrosoureas by the reaction of N-nitroso-N-alkylcarbamoylazide with a diamine, amino-alcohol or amino acid derivative is known from German Pat. No. 26 23 420.

It has now been found that analogs of the clinically established chemotherapeutic agent CCNU (1-(2-chlorethyl-1-nitroso-3-(cyclohexyl)-urea), substituted by heterocyclic rings, amino or alkyl amino radicals, can be obtained which have likewise a tumor-inhibiting effect. Starting from N-(2-halogenethyl)-N-nitrosocarbamoylazide, which is likewise disclosed in Germ. Pat. No. 26 23 420, another group of interesting chemotherapeutics thus becomes available. The heterocyclic ring-substituted compounds of this invention are prepared from hydrazine and its derivatives or heterocyclic N-amino compounds, such as hexamethyleneimine or N-aminopiperidine, N-aminomorpholine and their derivatives. Moreover heterocyclic N-amino compounds comprising N, S or P as further hetero atoms are suitable reactants.

The new compounds correspond to the general formula:

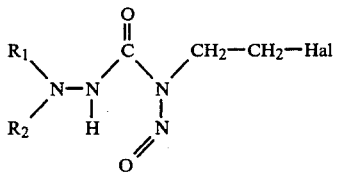

wherein $R_1$ and $R_2$ are selected from the group consisting of hydrogen, acyl, trifluoroacetyl, straight chained and branched alkyl groups with up to 6 carbon atoms, such alkyl groups with up to 3 substituents selected from the group consisting of OH, $OSO_2CH_3$, COOH, COOR, $CONH_2$ and Hal, where R is an alkyl group with up to 6 carbon atoms, and $R_1$ and $R_2$ together form a heterocyclic ring containing 4 to 6 carbon atoms and optionally further heteroatoms and such rings with up to 3 substituents selected from the group consisting of lower alkyl, OH, COOH, COOR, $CONH_2$, where R has the above meaning, the chloroethyl nitrosoureido group and Hal, and Hal is selected from the group consisting of chlorine and fluorine.

The general reaction for the preparative method is as follows:

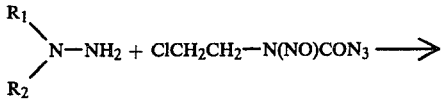

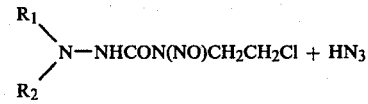

Some of the novel compounds can also be prepared in conventional manner according to the Johnston et al method, J. Med. Chem 9 892-911 (1966), (f.i. examples 9 and 10) which is as follows:

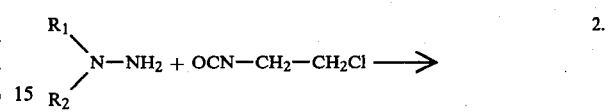

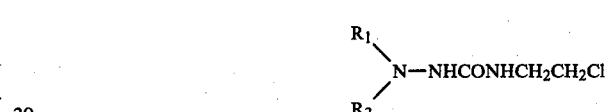

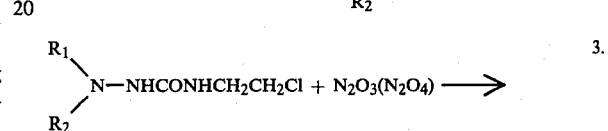

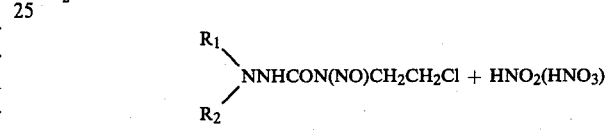

The following preparative examples will illustrate the invention:

EXAMPLE 1

1-(2-chloroethyl)-1-nitroso-3-(1-piperidine)urea

To a solution of 0.1 mole N-(2-chloroethyl)-N-nitrosocarbamoylazide in 75 ml dichloromethane is added in drops at −5 degC. (°C.) under stirring within 2 hours a solution of 0.2 mole N-aminopiperidine in 20 ml of a mixture of 4 parts by volume dichloromethane and 1 part by volume n-pentane. After the addition, the stirring is continued for one hour and a whitish-yellow precipitate is obtained. Subsequently it is shaken out with the same volume of 0.1 N $H_2SO_4$. The organic phase is dried over $Na_2SO_4$ and concentrated on the rotary evaporator. From ethyl formate/n-pentane we obtain on standing in the deep freezer yellow crystals which are homogeneous in thin-layer chromatography, after recrystallization from the same solvent mixture (silicagel foils, solvent system n-pentane/diethylether/dichloromethane 5:2:2)

Yield: 21%, fp: 88–89 degC. (°C.)

| elementary analysis: | calc. (%) | found (%) |
| --- | --- | --- |
| C | 40.94 | 41.28 |
| H | 6.44 | 6.64 |
| N | 23.87 | 23.91 |
| Cl | 15.10 | 15.17 |

The spectroscopic data confirm the homogeneity and structure of the compound. Thus, the IR-spectrum (KBr-tablet) shows the typical bands at 3240 cm$^{-1}$ (NH), 1710 cm$^{-1}$ (CO), 1525 cm$^{-1}$ (CNH) and 1480 cm$^{-1}$ (NO). In the NMR-spectrum (D$_6$-acetone), the NH signal appears at delta=8.9 ppm (broad, D$_2$O-exchangeable), the typical downfield triplet of the nitrosated chloroethylureido-structural element is at delta=4.17 ppm (CH$_2$—NNO), the upfield triplet at delta=3.60 ppm (Cl—CH$_2$). Characteristic fragments in the mass spectrum (70 ev) are in the upper mass range at m/e 204 (M-NO)+ with a peak ratio of 3:1 to the isotope peak typical of monochloro-compound at m/e 206, at m/e 126 (M-Cl(CH$_2$)$_2$N$_2$OH* and at m/e 99 (M-CON$_2$O(CH$_2$)$_2$Cl). The substance shows the typical color reaction to N-nitroso compounds, (G. Eisenbrand, R. Preussmann, Arzneimeittelforsch, No. 20, 1513 (1970).

Animal test results show a very good effectiveness in rat leukemia L 5222.

EXAMPLE 2

1-(2-chloroethyl)-1-nitroso-3-(4-morpholino)-urea

To a solution of 0.1 mole N-(2-chloroethyl)-N-nitrosocarbamoylazide in 75 ml dichloromethane is added in drops at −5 degC. under stirring within 2 hours a solution of 0.2 mole N-aminomorpholine in 20 ml of a mixture of 4 parts by volume dichloromethane and 1 part by volume n-pentane. The further preparation is as described in example 1. From n-pentane/dichloromethane are obtained light-yellow crystals which are homogeneous in thin-layer chromatography, after recrystallization from ethyl formate/n-pentane (silicagel foils, solvent system as in example 1).

Yield: 40%, mp: 77-78 degC.

| Elementary analysis: | Calc. (%) | Found (%) |
|---|---|---|
| C | 35.53 | 35.59 |
| H | 5.54 | 5.79 |
| N | 23.67 | 23.38 |
| Cl | 14.98 | 14.75 |

Spectroscopic data confirm the homogeneity and structure of the compound. The IR-spectrum shows for the nitrosoureas typical bands at 3205 cm$^{-1}$ (NH), 1710 cm$^{-1}$ (CO), 1525 cm$^{-1}$ (CNH) and 1480 cm$^{-1}$ (NO). In the NMR-spectrum (D$_6$-acetone) the NH-signal is at delta=9.1 ppm (broad, D$_2$O exchangeable) the downfield triplet of the nitrosated chloroethyl structural element is at delta=4.17 ppm (CH$_2$—NNO), the upfield triplet, partly overlapping with the signals of the CH$_2$ groups in position 2 and 4 of the morpholine ring, is at delta=3.60 ppm (Cl—CH$_2$). Characteristic fragments in the mass spectrum (70 ev) are at m/e 206 (M-NO)+ with the peak ratio of 3:1 to the isotope peak, typical of monochloro-compounds, at m/e 208, at m/e 128 (M-Cl—(CH$_2$)$_2$N$_2$OH)+ and at m/e 101 (M-CON$_2$O(CH$_2$)$_2$Cl)+. The substance shows the typical color reaction to N-nitroso compounds.

Animal test results show very good effectiveness in rat leukemia L 5222. Unlike the clinically established substance CCNU the compound is highly water-soluble. Among others it was tested on the Yashida sarcoma of the rat implanted in the colon, and shows there better therapeutic results than e.g. the compound methyl-CCNU used clinically in colon tumors (cf. example 12).

EXAMPLE 3

1-(2-chloroethyl)-1-nitroso-3-(4-(2,6-dimethyl morpholino)-urea

To a solution of 0.02 mole N-(2-chloroethyl)-N-nitrosocarbamoylazide in 15 ml dichloromethane is added in drops at −5 degC. under stirring within 2 hours 0.04 mole 4-amino-2,6-dimethyl morpholine in 20 ml dichloromethane. After stirring for another hour, the product is treated as in example 1. From dichloromethane/n-pentane are obtained light-yellow crystals which are homogeneous in thin-layer chromatography after recrystallization.

Yield, 45% mp: 102-104 degC.

Spectroscopic data confirm the homogeneity and structure of the compound.

The IR-spectrum (KBr-tablet) shows the typical nitrosourea bands (NH, CO, CNH, NO). In the NMR-spectrum (D$_6$-acetone), the NH-signal appears at delta=9 ppm, the typical downfield triplet of the nitrosated chloroethyl nitroso-ureido structural element is at delta=4.17 (CH$_2$—NNO) the upfield triplet, partly overlapped by the ring-CH-signals in position 2 and 6, is at delta=3.60 ppm. The signal of the methyl groups in position 2 and 6 of the morpholino ring appears at delta=1.15 ppm. The substance shows the typical color reaction to N-nitroso compounds.

EXAMPLE 4

1-(2-chloroethyl)-1-nitroso-3-dimethylaminourea

To a solution of 0.05 mole N-(2-chloroethyl)-N-nitroso-carbamoylazide in 15 ml isopropanol/carbon tetrachloride is added in drops at −10 degC. under stirring 0.1 mole dimethyl hydrazine in 10 ml isopropanol so slowly that the pH-value does not rise above 7.5 (3 hours reaction time). After stirring for another hour, the mixture is acidified with diluted sulfuric acid and shaken out with ethyl formate. The organic phase is dried over Na$_2$SO$_4$ and concentrated. The crude product was purified by column chromatography on a commercial silicagel column (solvent system ether/ethanol 98:2). After withdrawing the solvent, an oily residue remained, which was homogeneous in thin-layer chromatography.

Yield 20%

The NMR spectrum (D$_6$-acetone) confirms the homogeneity and structure of the compound. The NH-signals appears at 8.9 ppm. The downfield triplet of the nitrosated chloroethyl nitrosoureido-structural element is at delta=4.17 (CH$_2$NNO), the upfield triplet at delta=3.60 ppm. The signal of the methyl groups appears at delta=2.75 ppm. The substance shows the typical color reaction to N-nitroso-compounds.

EXAMPLE 5

1-(2-chloroethyl)-1-nitroso-3-hexamethyleneiminourea

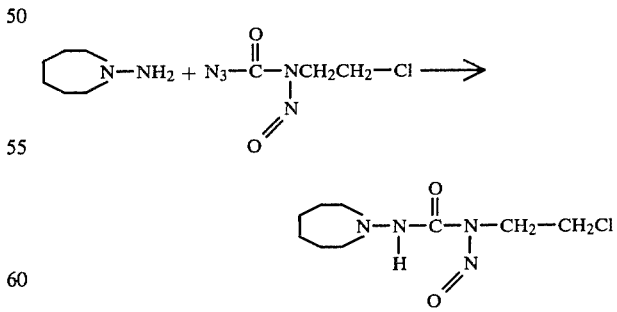

0.05 mole N-(2-chloroethyl)-N-nitroso-carbamoylazide are dissolved in dichloromethane and cooled to −10° C.

To this solution are slowly added in drops 10 g (0.09 mole) N-aminohexamethyleneimine in 10 ml dichloromethane.

After stirring for one hour, it is shaken out with the same volume 0.1 N H$_2$SO$_4$, subsequently with water. The organic phase is dried over Na$_2$SO$_4$ and subsequently the solvent is withdrawn.

The crude product is purified by column chromatography on silica gel with the solvent system pentane/ether/dichloromethane 5:2:2 and is obtained, after concentration, in the form of light yellow crystals, which are homogeneous in thin-layer chromatography.

Yield: 20% (after column chromatography)
Melting point: 35°–36° C.;

Spectroscopic data confirm homogeneity and structure. In the NMR-spectrum (d$_6$ acetone) the NH-signal appears at δ=9.10 ppm (broad, D$_2$O exchangeable), the downfield-triplet of the 2-chloroethyl-N-nitrosoureido group is at δ=4.15 ppm (CH$_2$NNO), the upfield-triplet is at δ=3.55 ppm (ClCH$_2$). The signals of the ring protons are at 2.80–3.28 ppm (4 protons) and at 1.65 ppm (6 protons).

The substance shows the typical color reaction to N-nitroso compounds

EXAMPLE 6

1-(2-chloroethyl)-1-nitroso-3-(1-(4-methyl-piperidino)urea

To a solution of 0.02 mole N-(2-chloroethyl)-N-nitroso-carbamoylazide in 15 ml dichloromethane are added in drops 0.04 mole 1-amino-4-methylpiperidine in 20 ml dichloromethane at −5° C., under stirring within about 2 hours. After further stirring for one hour, it is shaken out with the same volume 0.1 N H$_2$SO$_4$ and subsequently with water. The acid aqueous phase collected is re-extracted once with dichloromethane. The combined organic phase is dried over Na$_2$SO$_4$, subsequently the solvent is withdrawn on the rotary evaporator.

The crude product is subsequently purified by column chromatography on silica gel with the solvent system pentane/ether/dichloromethane 6:1:2 and, after concentration, is obtained in the form of light yellow crystals, which are homogeneous in thin layer chromatography.

Yield: 77% (crude product); Melting point: 89°–91° C.

Spectroscopic data confirm homogeneity and structure. In the NMR-spectrum (D$_6$-acetone) the NH-signal appears at δ=8.8 ppm (broad, D$_2$O-exchangeable), the typical downfield-triplet of the nitrosated 2-chloroethylnitrosoureido structural element is at δ=4.12 ppm (CH$_2$NNO), the upfield-triplet is at δ=3.57 ppm (Cl-CH$_2$). The signal of the 4-methyl group appears at δ=0.95 ppm, signal groups for the ring protons are at 0.90–1.20 ppm as well as at 2.60–3.20 ppm. The substance shows the typical color reaction to N-nitroso compounds.

EXAMPLE 7

1-(2-chloroethyl)-1-nitroso-3-(1-(4-hydroxypiperidino)urea

To a solution of 0.004 mole N-(2-chloroethyl)-N-nitrosocarbamoylazide in 3 ml dichloromethane are added slowly dropwise 0.008 mole 1-amino-4-hydroxypiperidine in 5 ml dichloromethane at −5° C. under stirring. After further stirring for one hour, it is acidified with 0.1 N H$_2$SO$_4$ to pH 1 and subsequently shaken out with water. The collected aqueous acid phase is re-extracted twice with dichloromethane. The combined organic phase is dried over Na$_2$SO$_4$, subsequently the solvent is withdrawn on the rotary evaporator. The crude product is purified by column chromatography on silica gel with the solvent system chloroform/methanol 9:1 and is, after concentration, obtained in the form of light yellow crystals, which are homogeneous in thin-layer chromatography.

Yield: 30%
Melting point: 88°–90° C.

Spectroscopic data confirm the homogeneity and structure. In the NMR-spectrum (D$_6$-acetone) the NH-signal appears at δ=7.84 ppm (D$_2$O exchangeable), the typical downfield triplet of the nitrosated 2-chloroethylnitrosoureido structural element is at δ=4.18 ppm (CH$_2$ N NO), the upfield triplet is at δ=3.51 ppm (Cl-CH$_2$). The signal of the 4-hydroxy group appears at δ=2.09 ppm (D$_2$O exchangeable).

The ring proton in the proximity of the hydroxyl group provides a multiplet at δ=3.87 ppm. The signal groups for the rest of the ring protons appear at δ=2.70–3.33 ppm as well as at δ=1.56–2.30 ppm.

The substance shows the typical color reaction to N-nitroso compounds.

EXAMPLE 8

1-(2-chloroethyl)-1-nitroso-3-amino-urea = 1-(2-chloroethyl)-1-nitrososemicarbazide

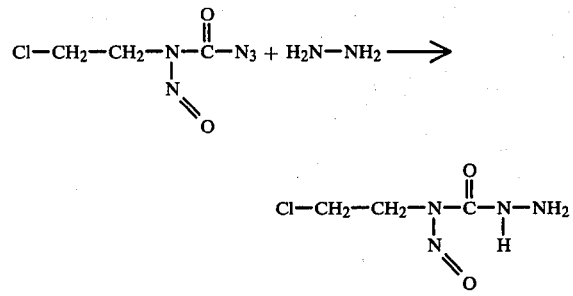

0.1 mole N-(2-chloroethyl)-N-nitroso-carbamoylazide are dissolved in ethanol at −10° C.

To this solution are slowly added dropwise 0.7 mole (7 g) hydrazine hydrate in 20 ml ethanol.

A lively reaction takes place with a white deposit precipitating out with increasing duration. The pH is controlled and does not rise to above 6. After addition has been completed, the deposit is sucked off, the filtrate is weakly acidified with diluted sulfuric acid, is mixed with water and is shaken out with ethyl formate.

The organic phase is dried and the solvent is withdrawn. The slightly stable substance can in this form be further reacted and stabilized, e.g. by reaction with a carbonyl compound.

Purification of the substance itself takes place via the precipitation as sulfate. To that end, 0.02 mole (3.2 g) of the compound are mixed at −10° C. with a mixture of 2 g H$_2$SO$_4$ (98%) in 3 g of water. The sulfate precipitates in that regard as yellow deposit. Said deposit is sucked off, is washed with water and is suspended in water. By careful addition of diluted NaOH up to a pH of 7.5, the compound is liberated from the sulfate and is dissolved. It is shaken out with dichloromethane, the organic phase is dried and concentrated. An oily residue remains, which is stable for a few days when stored in the deep freezing compartment at −30° C. The substance is homogeneous in thin-layer chromatography (in dichloromethane/methanol 9:1) and shows the typical color reaction of N-nitroso compounds.

Spectroscopic data confirm the uniformity and structure. In the NMR-spectrum (D5-pyridine), the NH-signal appears at $\delta=9.50$ ppm, the two triplets of the chloroethyl group appear at $\delta=4.28$ and 3.64 ppm, the signal of the NH2-group, very broad, appears at $\delta=4.5-6.8$ ppm. All three NH protons are D2O-exchangeable.

Yield: 45% (crude product)

EXAMPLE 9

1-(2-chloroethyl)-1-nitroso-3-(methyl-formyl-amino)urea = 1-methyl-1-formyl-4-nitroso-4(2-chloroethyl)-semicarbazide (a) 1-(2-chloroethyl)-3-(methyl-formyl-amino)urea = 1-methyl-1 formyl-4(2-chloroethyl) semicarbazide

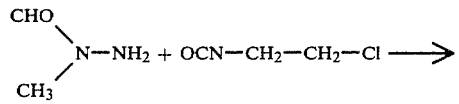

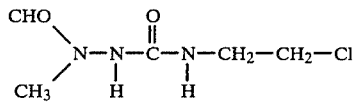

15.7 g (0.2 mole) 1-methyl-1-formyl-hydrazine are dissolved in absolute ether.

21.1 g (0.2 mole) 2-chloroethylisocyanate, dissolved in ether, are added dropwise under cooling.

The urea precipitates out as white deposit.
Yield: 31 g = 86%
Melting point: 64°-66° C.

(b) Nitrosation

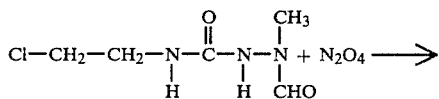

25 g Na-acetate are suspended in 100 ml glacial acetic acid and cooled to +10° C.

To this suspension are added 20 g N2O4.

10 g of the compound to be nitrosated are added spatulawise at 10° C. under stirring.

It was still subsequently stirred for 1 hour and then poured onto icewater.

The excess nitrite is removed with amidosulfonic acid and subsequently thereto it is shaken out with ethyl formate. The organic phase is dried and concentrated.

In the refrigerator, the end product crystallizes out. It is sucked off and washed with water.

Yield: 6.2 g = 53%

Melting point: 120°–21° C.

Spectroscopic data confirm homogeneity and structure. In the NMR-spectrum (d6acetone) the NH-signal appears at 10.46 ppm (D2O exchangeable), the downfield triplet of the 2-chloroethylnitrosoureido group is at $\delta=4.20$ ppm, the upfield triplet is at $\delta=3.60$ ppm.

The signal of the formyl CH-proton appears as sharply defined singlet at $\delta=8.19$ ppm. The methyl group appears with 2 singlets at $\delta-3.30$ and at 3.12 ppm (syn. anti). The substance shows the typical color reaction to N-nitroso compounds.

EXAMPLE 10

1-(2-chloroethyl)-1-nitroso-3-(methyl-acetyl-amino)urea = 1-methyl-1-acetyl-4-nitroso-4(2-chloroethyl)-semicarbazide. According to the procedure of example 9 0.2 mole 1-methyl-1-acetyl-hydrazine are reacted with 0.2 mole 2-chloroethylisocyanate and the precipitate obtained is treated with N2O2 to form the desired reaction product in a yield comparable to that of example 9.

Just as the other new compounds within the scope of the above general formula, the compounds wherein R2 is acyl such as formyl or acetyl also have excellent tumor-inhibiting properties as is seen from the following examples.

EXAMPLE 11

Chemotherapeutic activity of methylformylamino-CNU against rat Leukemia L5222 (CNU = chloroethyl-nitroso-urea)

The compound to be tested was solved in Chremophor EL/ethanol/physiological saline and a single dose was administered intraperitoneally into tumor inoculated BD IX rats. The experiment involved an untreated control group and a number of treated groups. The doses used and the effects of the praeterminal treatment are summarized in the following Table from which the cures (animals free of tumor after 120 days) and the increase in life span (ILS, expressed as percentage of survival of the treated test group to the untreated control group) are evident.

| % ILS (cures) | 70 (⅜) | 100 (2/8) | 150 (2/8) | 175 (⅜) | 150 (2/8) | 610 (3/9) | 230 (2/6) | 250 | 40 |
|---|---|---|---|---|---|---|---|---|---|
| Dose (mg/kg) | 7 | 11,1 | 17,6 | 279 | 44,2 | 70 | 88 | 111 | 176 |

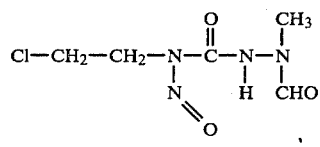

The results indicate that methylformylamino-CNU is active against rat Leucemia L5222 and results in about 30 to 40% cures in an extremely broad dosage of 7 to 176 mg/kg. Even the lowest dose of 7 mg/kg caused three cured animals out of eight.

EXAMPLE 12

The chemotherapeutic activity of nitrosoureas was compared in antitumor tests using Yoshida sarcoma ascited cells implanted into the wall of the descending colon in Sprague-Dawley rats. It was shown previously that this tumor responds favorably to cyclophosphamide treatment. BCNU and MeCCNU proved to be active against Yoshida sarcoma cells implanted into the colon wall after intraperitoneal application.

Cyclophosphamide is a well established drug in clinical use the structure and mode of action of which is different from those of nitroso-ureas. BCNU (1,3-bis-(2-chlorethyl)-1-nitrosourea) and MeCCNU (1-(2-chloroethyl)-3-(4-methylcyclohexyl)-1-nitrosourea) are also established drugs in clinical use and MeCCNU is considered the nitrosourea of first choice for gastrointestinal tumors. The present study is concerned with the effect of nitrosoureas according to the invention compared with these established drugs.

Male Sprague-Dawley rats were used in the experiments. Yoshida sarcoma in ascites form was maintained in the same strain of rats by serial intraperitoneal injection of 0,5 ml of ascites fluid.

$3 \times 10^6$ cells were injected into the colon wall in a manner known per se. The chemotherapeutic treatment was carried out on the eighth day after implantation of the tumor cells.

Water-insoluble compounds were dissolved in Cremophor EL/ethanol/physiological saline (20:20:60: vol.%). Water-soluble substances were dissolved in physiological saline. Cremophor EL is a surfactant on the basis of polyethoxylated castor oil. All test compounds were administered introperitoneally. The nitrosoureas were applied at approximately equitoxic doses corresponding to about 80% of the acute $LD_{50}$ values observed in healthy rats of the same strain over a 28-day observation period.

Each experiment involved an untreated control group and a varying number of treated groups. Individual survival times were counted as days after tumor inoculation. At the time of death a record of whether an animal was tumor-free or not was made. All animals alive 120 days after tumor inoculation were killed. Animals that according to macroscopic examination had no tumor at the end of the experiment were considered as cured. Since in a number of control rats also no tumors occurred after 120 days the differences in cures between controls and treated animals rather than absolute numbers are reported. Differences in survival were evaluated statistically by individual comparisons between treated rats and controls using a nonparametric log-rank test (Kalbfleisch and Prentice, The statistical analysis of failure time data, Wiley, New York, 1979). Numerical evaluation was performed using a computerized system.

Figure 2:
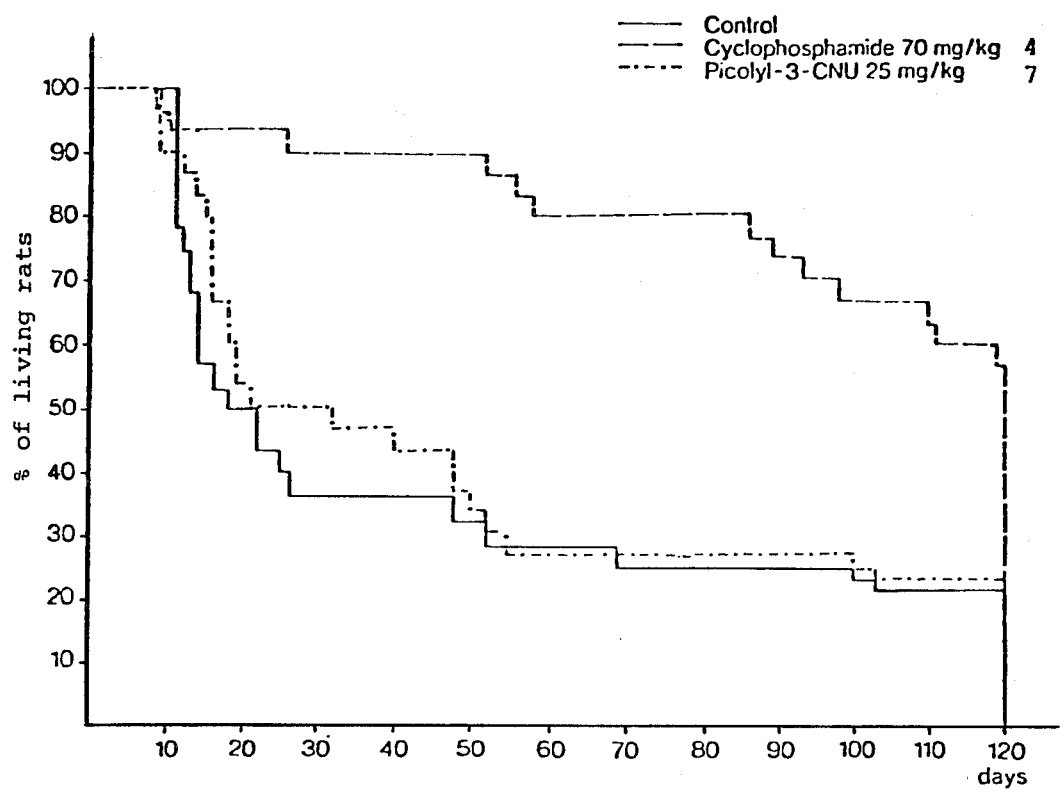
Figure 3:
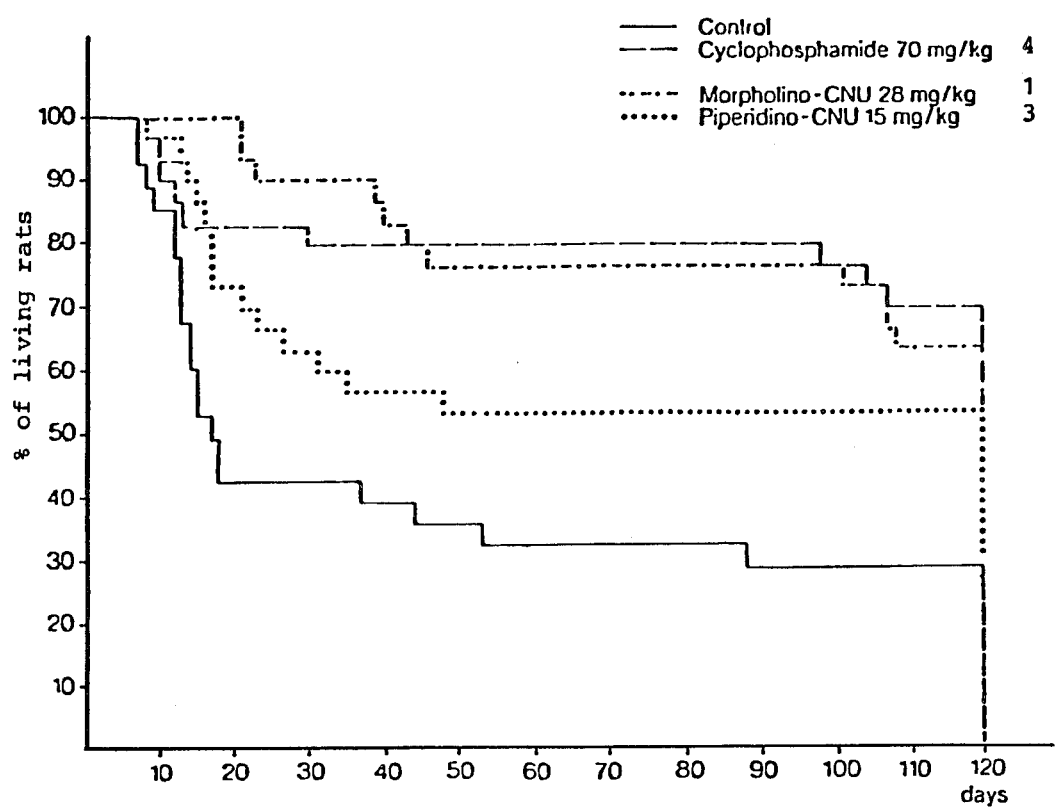
Figure 4:
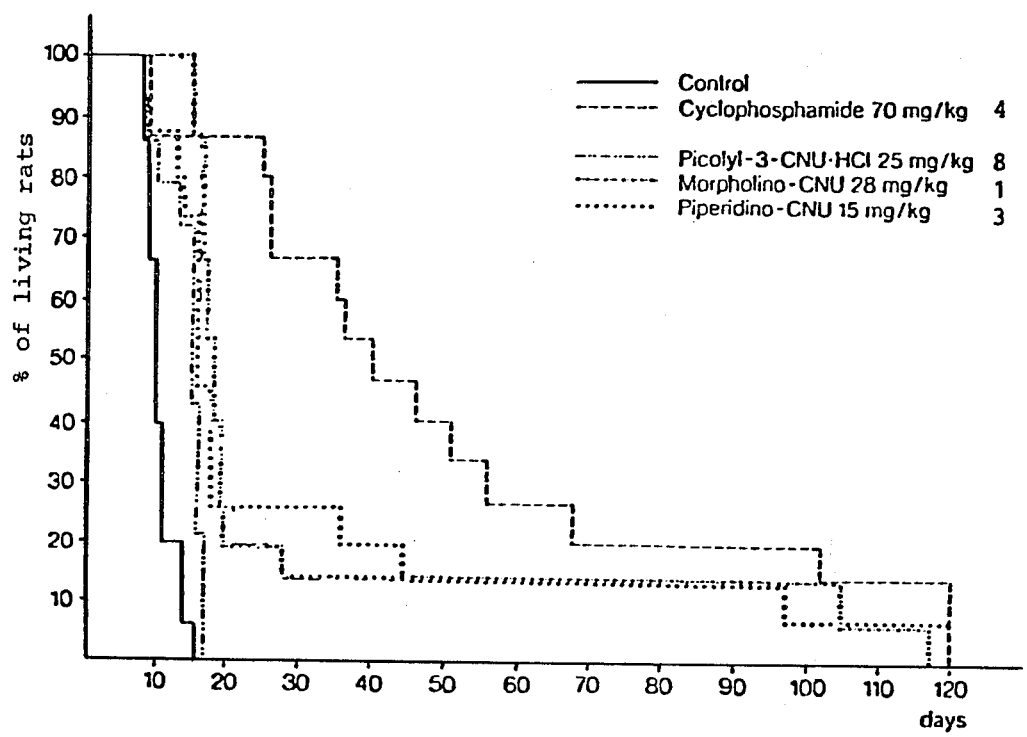

Table 1 lists the structures, chemical names, and abbreviations of the tested compounds. The results of the chemotherapy experiments are summarized in tables 2 and 3 and FIGS. 1 to 4.

From experiments 1, 2 and 3 it can be concluded that cyclophosphamide was the most active compound. In comparison with controls the frequency of cures (25 to 38%) was higher and the survival time of treated rats improved significantly ($p<0,05$). BCNU and MeCCNU also increased the number of tumor-free animals observed on day 120 (increase: 18 and 8% above controls, respectively), but this did not result in a significant increase in life expectancy. Since 19% of the MeCCNU-treated animals died without a tumor before day 120, MeCCNU was obviously toxic at the dose tested (45 mg/kg).

Morpholino-CNU exhibited a clear chemotherapeutic activity in both experiments (3 and 5). The dose of 28 mg/kg improved the survival times significantly and resulted in a large number of tumor-free animals at the end of the experiments. In this experimental model the chemotherapeutic activity and toxicity of morpholino-CNU were similar to those of cyclophosphamid.

Dimethylmorpholine-CNU administered at a dose of 45 mg/kg significantly improved the life expectancy of the treated animals ($p<0,05$) and at the end of the observation period 20% more treated rats proved to be tumor-free compared with the controls.

Piperidino-CNU administered at a dose of 15 mg/kg significantly increased the survival time, and after 120 days 21% more animals were tumor-free compared with the controls. No toxic effects were seen at this dose.

Picolyl-3-CNU administered at a dose of 25 mg/kg produced only an insignificant increase in life expectancy, and after 120 days less animals proved to be tumor-free compared with the controls.

Picolyl-3-CNU.HCl applied at a dose of 25 mg/kg increased the rate of tumor-free animals to 15% above the controls without resulting in a significant increase in survival.

Some of the promising compounds were retested in experiment 5 using cyclophosphamide as a standard. A significant increasing effect on the survival time was again seen for morpholino-CNU and piperidino-CNU but not for picolyl-3-CNU-HCl.

In all treated animals and at all doses tested the mean weight gain was lower than in the controls. Table 3 gives the mean animal weights measured 50 and 100 days after tumor transplantation in experiments 1 to 5.

In the present series of experiments, the successful takes in untreated animals ranged from 71 to 100%. In experiment 5 there was noted a transplant take rate of 100%. The tumor growth was highly invasive and killed the untreated animals after a median introduction time of 10 days. After 120 days, only 1/15 (7%) of the animals injected with cyclophosphamide (70 mg/kg) was tumor-free. In the other experiments the rates of tumor-free animals treated with cyclophosphamide were 50, 57 and 67%. The biological behavior of the tumors also differed considerably from experiment to experiment. Therefore, each experiment was allotted its own control and standard therapy group (cyclophosphamide).

The results obtained with established clinical drugs, e.g. cyclophosphamide, correspond to previous experiences. The experiments, in which BCNU and MeCCNU were administered at a single high dose, confirmed that tumor-bearing animals are less resistant to the toxicity of nitrosourceas than healthy animals. BCNU and MeCCNU increased the rate of tumor-free animals alive at the end of the experiment, but did not lead to a significant increase in survival time.

Out of the water-soluble test compounds according to the invention morpholino-CNU, dimethylmorpholino-CNU, and piperidino-CNU proved to be active. The present investigation confirmed the assumption that the cytostatic activity of nitrosoureas is not merely a function of water-solubility because other water-soluble CNU-compounds were practically ineffective. Among the water-insoluble comparative compounds tested, picolyl-3-CNU exerted only marginal activity at the administered doses.

In the present tumor model morpholino-CNU, piperidino-CNU and dimethylmorpholino-CNU, reached the distal colon at chemotherapeutically effective concentrations. Their administration induced a remarkable increase in tumor-free animals alive at the end of the observation period (120 days) and a significant increase in survival time. At the doses tested piperidino-CNU was less toxic than cyclophosphamide. The toxic and chemotherapeutic effects of dimethylmorpholino-CNU seem to be similar to those of morpholino-CNU.

The present results clearly show the superiority of the compounds according to the invention over known clinically established nitrosoureas.

TABLE 1

| No. | Structure | Chemical name | Abbreviation used |
|---|---|---|---|
| 1 | CNU—N(morpholino ring) | 1-(2-chloroethyl)-1-nitroso-3-(4-morpholino)-urea | morpholino-CNU |
| 2 | CNU—N(2,6-dimethylmorpholino ring) | 4[1-(2-chloroethyl)-1-nitroso]-3-[4-(2,6-dimethylmorpholino)]-urea | dimethylmorpholino-CNU |
| 3 | CNU—N(piperidino ring) | 1-(2-chloroethyl)-1-nitroso-3-(1-piperidino)-urea | piperidino-CNU |
| 4 | cyclophosphamide structure with P=O, O, N(CH$_2$CH$_2$Cl)$_2$, NH | cyclophosphamide = 2-bis-($\beta$-chloroethyl)-amino-oxo-2-oxa-2-$\lambda^5$-phospha-3-aza-cyclohexane | CP |
| 5 | Cl—CH$_2$—CH$_2$—CNU | 1,3-bis-(2-chloroethyl)-1-nitrosourea | BCNU |
| 6 | CH$_3$—(cyclohexyl)—CNU | 1-(2-chloroethyl)-3-(4-methylcyclohexyl)-1-nitroso-urea | MeCCNU |
| 7 | CNU—CH$_2$—(3-pyridyl) | 1-(2-chloroethyl)-1-nitroso-3-(methylene-3-pyridyl)-urea | picolyl-3-CNU |
| 8 | (pyridinium)—CH$_2$—CNU·HCl | [1-(2-chloroethyl)-1-nitroso-3-(methylene-3-pyridilium)-ureido]-chloride | picolyl-3-CNU·HCl |

TABLE 2

Results of the chemotherapy with the compounds tested

| No. | Substance Abbreviation | Solvent* | Dose (mg/kg) | M days | % M | p | tf$_{120}$ No. (%) | D$_{120}$ % | tf$_{1-120}$ No. (%) | D$_{1-120}$ % | Initial number of animals |
|---|---|---|---|---|---|---|---|---|---|---|---|
| | Experiment 1: | | | | | | | | | | |
| | Untreated control | — | — | 46 | 100 | | 7(25) | — | 7(25) | — | 28 |
| 4 | CP | sal | 70 | >120 | >260 | + | 15(50) | 25 | 21(63) | 38 | 30 |
| 5 | BCNU | surf | 25 | '74 | 160 | | 13(43) | 18 | 14(47) | 22 | 30 |
| 6 | MeCCNU | surf | 45 | 60 | 130 | | 10(33) | 8 | 15(52) | 27 | 29 |
| | Experiment 2: | | | | | | | | | | |
| | Untreated control | — | — | 22 | 100 | | 6(22) | — | 6(22) | — | 27 |
| 4 | CP | sal | 70 | >120 | >545 | + | 17(57) | 35 | 24(80) | 58 | 30 |
| 7 | Picolyl-3-CNU | surf | 25 | 28 | 130 | | 6(20) | −2 | 7(23) | 1 | 30 |
| 8 | Picolyl-3-CNU.HCl | sal | 25 | 27 | 125 | | 11(37) | 15 | 12(40) | 18 | 30 |
| | Experiment 3: | | | | | | | | | | |
| | Untreated control | — | — | 17.5 | 100 | | 8(29) | — | 8(29) | — | 28 |
| 4 | CP | sal | 70 | >120 | >686 | + | 20(67) | 38 | 23(77) | 48 | 30 |
| 1 | Morpholino-CNU | sal | 28 | >120 | >686 | + | 19(63) | 34 | 21(70) | 41 | 30 |
| 3 | Piperidino-CNU | sal | 15 | >120 | >686 | + | 15(50) | 21 | 15(50) | 21 | 30 |
| | Experiment 4: | | | | | | | | | | |
| | Untreated control | | — | 19 | 100 | | 6(20) | — | 6(20) | — | 30 |

TABLE 2-continued

Results of the chemotherapy with the compounds tested

| No. | Substance Abbreviation | Solvent* | Dose (mg/kg) | M days | % M | p | tf$_{120}$ No. (%) | D$_{120}$ % | tf$_{1-120}$ No. (%) | D$_{1-120}$ % | Initial number of animals |
|---|---|---|---|---|---|---|---|---|---|---|---|
| 2 | Dimethylmorpholino-CNU | sal | 45 | 71 | 374 | + | 12(40) | 20 | 14(47) | 27 | 30 |
| | Experiment 5: | | | | | | | | | | |
| | Untreated control | — | — | 10 | 100 | | 0 | — | 0 | — | 15 |
| 4 | CP | sal | 70 | 40 | 400 | + | 1(7) | 7 | 1(7) | 7 | 15 |
| 8 | Picolyl-3-CNU.HCl | sal | 25 | 15 | 150 | | 0 | 0 | 0 | 0 | 14 |
| 1 | Morpholino-CNU | sal | 28 | 18 | 180 | + | 0 | 0 | 0 | 0 | 15 |
| 3 | Piperidino-CNU | sal | 15 | 16 | 160 | + | 1(7) | 7 | 2(13) | 13 | 15 |

M = median survival time

% M = median life expectancy of treated animals versus controls $\frac{M_{treat.}}{M_{untreat.}} \times 100$ p = probability of error <5% (log-rank test comparison of survival time) + indicates that the survival time of treated animals is different from the controls
tf$_{120}$ = animals surviving day 120 without tumor
D$_{120}$ = difference (%) between tf$_{120}$ of treated and untreated animals
tf$_{1-120}$ = animals dying without tumor over the whole experimental time, i.e. tf$_{120}$ + animals dying of toxicity
D$_{1-120}$ = difference (%) between tf$_{1-120}$ of treated and untreated animals
Solvent:
sal = physiological saline
surf = surfactant

TABLE 3

Mean animal weight recorded 50 and 100 days after tumor transplantation

| Experiment | Drug | Dose administered (mg/kg) | Weight (g) on day 50 | Weight (g) on day 100 |
|---|---|---|---|---|
| 1-5 | untreated control | — | 330-380 | 410-470 |
| 1-3 | CP | 70 | 300-330 | 300-370 |
| 1 | BCNU | 25 | 270 | 300 |
| | MeCCNU | 45 | 280 | 300 |
| 2 | picolyl-3-CNU | 25 | 250 | 250 |
| | picolyl-3-CNU.HCl | 25 | 250 | 260 |
| 3 | morpholino-CNU | 28 | 270 | 270 |
| | piperidino-CNU | 15 | 340 | 410 |
| 4 | dimethyl-morpholino-CNU | 45 | 250 | 250 |

The above test results show that generally all types of tumors are effectively treated with the compounds according to the invention when used at doses of up to 80% of the acute LD$_{50}$ which is determined in healthy test animals. Considering the fact that the true measure of the effectiveness of a drug against a neoplastic desease is the ability of the drug to kill the neoplastic cells at dosages that are not toxic to the host animal and that a quantitative evaluation of drug action is usually obtained by using the L1210 leucemia system in mice, it will be realized that in this test the tumor cells are injected into the peritoneal cavity of a mouse which thereafter is treated with the drug to be tested at a very early time after the inoculation of the tumor, i.e. at the first or second day after tumor inoculation. Thus such screening is done under very favourable test conditions for the drug. Contrary thereto the administration of the drug to be tested is performed relatively late in the case of the rat leucemia L5222, i.e. at the 8th day after tumor inoculation. It must, therefore, be taken that at that time tumor cells have colonized the cerebral region, i.e. the meninges, so that cures can only be obtained if the drug has an activity high enough to kill the leucemia cells in the cerebral region in a praeterminal state. Thus by far more severe test conditions are involved when treating rat leucemia L5222 or type Yoshida sarcoma which is a tumor model and which are hard to influence by known drugs. Compounds being active in those tests will generally be even more effective in treating the mouse leucemia L1210 and other tumor models generally used for screening.

What is claimed is:

1. 1,3-Disubstituted nitroso ureas of the formula:

$$R_1 \underset{R_2}{\overset{}{\diagdown}} N - N \underset{H}{\overset{\overset{\displaystyle O}{\|}}{-}} C - N \underset{\underset{\displaystyle O}{\|}}{\overset{}{\diagdown}} CH_2 - CH_2 - Hal$$

wherein R$_1$ and R$_2$ are selected from the group consisting of hydrogen, acyl, straight chained and branched alkyl groups with up to 6 carbon atoms, and R$_1$ and R$_2$ together form a heterocyclic ring containing 4 to 6 carbon atoms and optionally further heteroatoms and such rings with up to 3 substituents selected from the group consisting of lower alkyl, OH, and Hal is selected from the group consisting of chlorine and fluorine, which heterocyclic ring is not the para-methyl piperazine group, said nitroso ureas having a tumor inhibiting effect.

2. A 1,3-disubstituted nitroso urea according to claim 1 comprising:
   1-(2-chloroethyl)-1-nitroso-3-(1-piperidino) urea.

3. A 1,3-disubstituted nitroso urea according to claim 1 comprising:
   1-(2-chloroethyl)-1-nitroso-3-(4-morpholino)-urea.

4. A 1,3-disubstituted nitroso urea according to claim 1 comprising:
   1-(2-chloroethyl)-1-nitroso-3-(4-(2,6-dimethyl morpholino)-urea.

5. A 1,3-disubstituted nitroso urea according to claim 1 comprising:
   1-(2-chloroethyl)-1-nitroso-3-dimethylaminourea.

6. A 1,3-disubstituted nitroso urea according to claim 1 comprising:
   1-(2-chloroethyl)-1-nitroso-3-hexamethyleneimino-urea.

7. A 1,3-disubstituted nitroso urea according to claim 1 comprising:
   1-(2-chloroethyl)-1-nitroso-3-(1-(4-methylpiperidino) urea.

8. A 1,3-disubstituted nitroso urea according to claim 1 comprising:

1-(2-chloroethyl)-1-nitroso-3-(1-(4-hydroxpiperidino)urea.

9. A 1,3-disubstituted nitroso urea according to claim 1 comprising:
1-(2-chloroethyl)-1-nitroso-3-amino-urea.

10. A compound according to claim 1 comprising:
1-(2-chloroethyl)-1-nitroso-3-(methyl-formyl-amino)urea.

11. A compound according to claim 1 comprising:
1-(2-chloroethyl)-1-nitroso-3-(methyl-acetyl-amino)urea.

* * * * *